United States Patent [19] [11] 4,111,778
Davis et al. [45] Sep. 5, 1978

[54] PROTECTION ASSEMBLY AND GROUND FOR GAS CONSTITUENT SENSOR

[75] Inventors: Donald Colen Davis, Fostoria; Alan H. Bilger, Tiffin; Kent Christ Madson, Jr., Kansas, all of Ohio

[73] Assignee: Bendix Autolite Corporation, Fostoria, Ohio

[21] Appl. No.: 857,333

[22] Filed: Dec. 5, 1977

[51] Int. Cl.[2] .............................................. G01N 27/46
[52] U.S. Cl. .................................. 204/195 S; 60/276; 123/119 E
[58] Field of Search .............. 204/195 S, 1 S; 60/276; 123/119 E; 324/29, 71 R

[56] References Cited

U.S. PATENT DOCUMENTS

| | | | |
|---|---|---|---|
| Re. 28,792 | 4/1976 | Ruka et al. | 204/1 T |
| 3,738,341 | 6/1973 | Loos | 123/119 R |
| 3,960,692 | 6/1976 | Weyl et al. | 204/195 S |
| 3,960,693 | 6/1976 | Weyl et al. | 204/195 S |
| 4,019,974 | 4/1977 | Weyl et al. | 204/195 S |
| 4,057,477 | 11/1977 | Weyl et al. | 204/195 S |

*Primary Examiner*—G. L. Kaplan
*Attorney, Agent, or Firm*—Gaylord P. Haas, Jr.

[57] ABSTRACT

A zirconia type oxygen partial pressure sensor for use with an exhaust system wherein an electrical voltage signal is generated in response to an oxygen partial pressure differential across a solid electrolyte. A reference oxygen partial pressure is introduced into the interior of a solid electrolyte sensor through an aperture formed in a housing for the sensor, a protective clip, wire mesh or spring being provided to at least partially cover the aperture to preclude contaminants from being introduced to the interior of the sensor through the aperture. A ground terminal assembly is also provided to supply a ground for the device in addition to that provided by the threaded engagement between the shell of the $O_2$ sensor and the exhaust system to which it is attached.

16 Claims, 12 Drawing Figures

2 80 86 94 96 92 68 20 22 26 24 44 46 2

2
80
86
94
96
92
68
20

22
26
24
44
46
2

80
86
72
82
92
90
68
62
64
60
58
20
30
76
70
48
52
38
22
26
40
24
34
32
44
36
46
48

102
68
100
90

106
102

106
100

108

112
114
68
110
90

114

68

122
120
90
68

134
80
130
90
132

122
68
120

68
20
22
26
44
46

134
80
130
90
138
68
20
22
26
44
46

148
146

148
80
140
90
142
68
20
22
26
146
44
46

PROTECTION ASSEMBLY AND GROUND FOR GAS CONSTITUENT SENSOR

BACKGROUND OF THE INVENTION

1. Field of the Invention

The present invention is related to a gas constituent sensor for sensing the concentration of a preselected gas relative to a reference concentration and is more particularly related to an oxygen partial pressure sensor which is utilized to sense the concentration of oxygen relative to a reference gas and more particularly to indicate, through the sensing of oxygen concentration relative to a reference oxygen concentration, whether a combustible mixture was or may be combusted at stoichiometric mixture ratio.

2. Description of the Prior Art

It is known that a body of solid electrolyte, for example zirconium dioxide, which is exposed on one surface to a reference oxygen concentration and exposed on a second opposed surface to an oxygen concentration to be sensed may generate an electrical potential between the two surfaces which is indicative of the difference in oxygen concentration between the mixture being sensed and the reference mixture. Examples of such sensors may be found in U.S. Pat. Nos. 3,960,692 and 3,960,693, both issued June 1, 1976, U.S. Pat. No. 4,019,974 issued Apr. 26, 1977 and U.S. Pat. No. Re. 28,792, reissued Apr. 27, 1976, the disclosures of which are incorporated herein by reference.

By coating the surface of the zirconium dioxide, or other solid electrolyte body, which with a catalytic material, such as platinum, the sensor would generate a relatively large output signal whenever the combustion mixture is at an air/fuel ratio less than the stoichiometric mixture ratio for that fuel and will generate a relatively low signal whenever the mixture is at an air/fuel ratio greater than the stoichiometric mixture ratio for that fuel. Thus, a generally step function will be generated by the sensor, the step function going from a relatively high value to a relatively low value at stoichiometric air/fuel mixture ratio for increasing air/fuel ratios passing through stoichiometric.

Typically, as seen in the above referenced patents, the solid electrolyte is formed in the shape of a closed ended tube or a thimble, and the thimble is coated on the inside and outside with the metallic electrode, porous material, for example, platinum or palladium. The gas sensor is then inserted, particularly into the exhaust system of an internal combustion engine, whereby the exterior of the closed end tube or thimble is exposed to the heated exhaust gas created by the combustion of gases within the internal combustion engine, or is exposed to the incoming air/fuel mixture, and the interior of the close ended tube or thimble is exposed to atmospheric conditions. Thus, the sensor will generate a voltage that is proportional to the difference between the partial pressures of oxygen between the interior and exterior of the electrolyte thimble.

In order to vent the interior of the tube or thimble to atmosphere, it has been the practice to provide a vent hole either through the solid electrolyte, an end terminal, or through a protective sleeve attached to the electrolyte, the interior of the sleeve being in fluid communication with the interior of the thimble. Thus, atmospheric mixture is drawn to the interior of the sensor to provide the reference atmosphere partial pressure. Patents illustrating such sleeve venting are above referenced U.S. Pat. Nos. 3,960,692; 3,960,693 and 4,019,974.

It has been found with vent holes of this type being utilized to provide atmospheric reference oxygen to the interior of the sensor, it is possible that excess road splash, or other contaminant materials, may be drawn into the interior of the sensor through the vent and cause sensor failure due to the presence of the contaminant. Also, if sufficient contaminant exists, there may be substantial reduction in the effective area of the interior surface of the gas sensor thereby reducing the effectiveness in the sensor in producing a sufficient voltage to sense the difference in the above-noted partial pressures. A suggested solution to this problem has been to provide a silicone rubber boot over the end of the gas sensor and covering the vent hole thereby precluding splash from entering the vent hole. Such a protective boot is illustrated in above referenced U.S. Pat. No. 3,690,693. However, while the vent hole is protected, the sensor must operate in a high ambient heat environment which may cause failure of the silicon rubber boot.

It has further been found that it is desirable to provide additional positive ground to the vehicle in addition to that provided by threadably inserting the gas sensor into the exhaust system. While previous systems have provided a second positive ground, as shown in above referenced U.S. Pat. No. 4,019,974, these systems have been relatively complicated in that the separate terminal is electrically isolated from the exterior housing of the sensor. Further, separate terminals have been provided at the upper end of the gas sensor attached to a metallic portion of the sensor forming the housing. A conductor is then crimped onto the terminal, the terminal being rigidly fastened to the sensor and a leadout wire is provided for the second ground. This system is relatively complicated and expensive to that proposed by the system of the present invention.

SUMMARY AND OBJECTS OF THE INVENTION

In order to alleviate the possibility of contaminants being introduced into the interior of the gas sensor, it is proposed to provide a clip or mesh type element around an area of the sensor through which the apertures have been formed to provide a passageway for ambient atmospheric pressure to be introduced to the interior of the thimble-like solid electrolyte sensor.

It is well known to utilized oxygen sensors to control the air/fuel ratio of an internal combustion engine to ensure that the carbon monoxide and hydrocarbons due to incomplete combustion of the fuel charge in the internal combustion engine are minimized. Thus, the exhaust products emitted from an internal combustion engine are monitored in order to decrease air pollution by eliminating pollutants from the exhaust due to such incomplete combustion. This monitoring is done by electrochemical sensors to sense the quality of combustion by exposing the sensor to the exhaust gases.

The oxygen sensors to which the present invention relates utilize the principle of sensing oxygen partial pressure differentials through the use of an ion conductive solid electrolyte. These sensors are secured, typically, in the wall of the exhaust system of the engine whereby the exhaust gases pass over an exterior surface of the sensing element. Ambient air is used as a reference for comparing the partial pressure of the reference gas to the partial pressure of the sensed exhaust gas by introducing the ambient air to the interior of the sensor.

The solid electrolyte is covered, both on the interior surface and the exterior surface, with an electron conductive, porous layer such as platinum. Each electron conductive layer has a contact portion which is utilized to form the terminal for that particular layer. In the case of the present invention, one of the terminals is formed by the metallic shell by which the sensor is secured to the exhaust system of the internal combustion engine. In this case, the entire chassis of the vehicle forms the ground conductor for the sensor. The other conductor is formed by an internal terminal or electrode which has electrical contact with the interior electron conductive layer, the output from this internal terminal being supplied by an exterior terminal.

Specifically, the oxygen sensor is fabricated of a shell element which forms the mounting body for the oxygen sensor, the shell element being provided with a threaded portion and a hexagonal surface portion to permit attachment of the oxygen sensor into the exhaust system of an internal combustion engine. The operative portion of the sensor is provided with a solid electrolyte sensing element which is generally formed in a cup-like or thimble shape, the protruding end of the solid electrolyte sensing element being protected by a metallic shielding sleeve such as is described in the above-reference U.S. Pat. No. 3,835,012. The sensing element is coated on the interior and exterior surfaces thereof with a catalytic material, such as porous platinum, to provide the catalytic action required for the step function described above and also to form the electrodes for the oxygen sensor. The upper end of the oxygen sensor is provided with a protective metallic sleeve or housing which is formed with a plurality of apertures to provide a conduit for ambient air to be introduced to the interior of the electrolyte element. A suitable spring member and terminal element is included to incorporate an external terminal for the oxygen sensor, the other terminal being provided by the shell member.

In order to protect against contaminants entering the aperture formed in the metallic sleeve, several modifications of a clip element or wire mesh are described, to at least partially mask the aperture formed in the metallic sleeve. Also, several embodiments of terminal elements are described to provide a ground for the oxygen sensor in addition to that provided by the contact between the shell element and the exhaust system tubing.

Accordingly, it is one object of the present invention to provide an improved gas constituent sensor assembly.

It is another object of the present invention to provide an improved gas constituent sensor assembly having protection against contaminants entering the internal portions of the sensor.

It is still a further object of the present invention to provide an improved oxygen sensor which is simple to manufacture, easy to assemble, and reliable in use.

BRIEF DESCRIPTION OF THE DRAWINGS

Further objects, features and advantages of the present invention will become readily apparent from a reading of the following description and a study of the attached drawings in which.

DETAILED DESCRIPTION OF THE DRAWINGS

Figure 1:
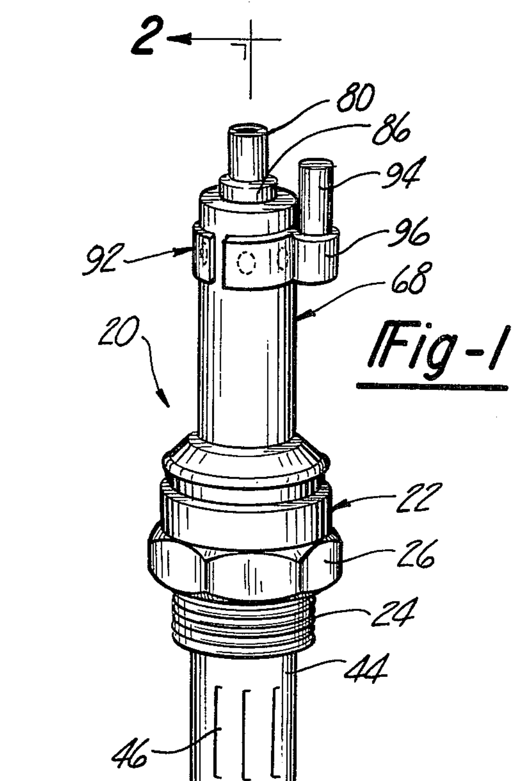
FIG. 1 is a perspective view of one form of the oxygen sensor incorporating certain features of the present invention.
Figure 2:
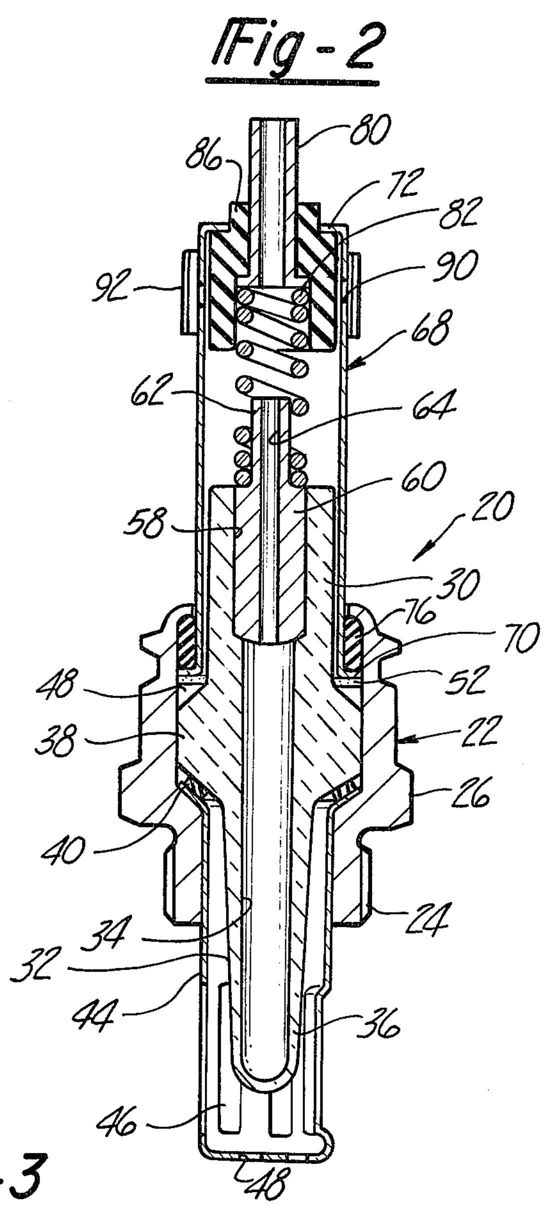
FIG. 2 is a cross-sectional view of FIG. 1 taken along line 2—2 thereof, and illustrating the interior configuration of the oxygen sensor.

Referring to the drawings, and particularly to FIGS. 1 and 2 thereof, there is illustrated an oxygen sensor 20 which takes the general shape of a spark plug. The oxygen sensor 20 includes a shell element 22 having formed thereon a threaded portion 24 which is adapted to threadedly engage the wall of the exhaust system of the internal combustion engine. The sensor 20 is tightened by means of a wrench applied to a hexagonal surface portion 26 to rigidly seat the sensor in the exhaust system.

The sensor 20 is provided with an ion conductive solid electrolyte tube element 30 which is formed generally as an elongated tube having an exterior surface 32 and an interior surface 34. The tube preferably is fabricated of zirconium dioxide, it being understood that other materials performing the same function may be substituted. The tube includes a closed end 36 which is adapted to be exposed to the exhaust gases of an internal combustion engine or, in the alternative, may be exposed to the intake fuel charge to the engine provide certain modifications are made to provide heat to the sensor. The electrolyte element 30 is coated on surfaces 32, 34 with porous electron conductive layers of platinum to form a catalyst for the gases exposed to the respective surfaces.

The electrolyte element 30 is formed with a shoulder portion 38, the lower surface of the shoulder portion being pressed into sealing engagement with a necked-down portion of the shell 22 through a metallic conductive washer element 40, the washer 40 preferably being formed from nickel, and a dished portion of a shielding sleeve 44. The shielding sleeve 44 is formed with a plurality of flutes 46 formed at the end thereof to permit exhaust gases to enter the interior of the sleeve 44 and come into contact with the conductive material formed on the surface 32 and the electrolyte element. The end of the shield 44 is formed with at least one aperture 48 to permit the exhaust gases within the sleeve 44 to exit back to the exhaust system. The flutes 46 are utilized to prevent direct impingement of contaminants in the exhaust gas on the end 36 of the solid electrolyte element 30. The operational purpose of the sleeve 44 is described in U.S. Pat. No. 3,835,012 issued Sept. 10, 1974, the disclosure of which is incorporated herein by reference.

During assembly, and after the sleeve 44, washer 40 and electrolyte element 30 are inserted into the shell 26, a talc ring 48 is inserted into the sleeve 22 and into engagement with the upper surface of the shoulder 38 for a seal. The talc ring eliminates the need for hot pressing to obtain a seal. Then a stainless steel washer 52, which it is believed it can be eliminated, is placed on top of the talc element 48 within the shell 22 and a downward compressive force between the shoulder 38 and the stainless steel washer 52 will compress the talc 48 to form a fluid tight seal between the electrolytic element 30 and the shell 22, thereby precluding exhaust gases from entering the upper portion of the sensing assembly 20.

The upper end of the electrolytic element 30 is provided with an enlarged bore 58, into which is inserted a conductive inner terminal element 60. The terminal element is preferably formed of stainless steel, as are other portions of the sensing assembly 20, to enable these elements to withstand the operating temperatures of the sensor. The inner terminal 60 is provided with a nipple 62, the terminal 60 being provided with a central bore 64 for purpose to be hereinafter explained.

The sensor assembly 20 is closed by means of a metallic housing sleeve 68 the sleeve being provided with an outwardly extending flange 70 and an inwardly extending flange 72. The outwardly extending flange 70 is placed in engagement with the nickel washer 52 and a stainless steel spacer collar 76 is provided between the sleeve 68 and the upper end of the shell 22. The upper end of the shell 22 is then forced over to create the compressive force necessary to seal the talc 48 and secure the entire lower assembly as a rigid unit.

The terminal 60 is in electrically conductive engagement with the platinum formed on the interior surface 34 to provide an inner electrical terminal for surface 34. This terminal is then extended to the exterior of the sensor by means of a stainless steel outer terminal 80 through an electrically conductive spring member 82 which is held in position at one end by nipple 62 and the other end by the cupped portion of an insulating spacer 86. Thus, the spring member provides the conductive lead to the terminal 80 and also provides the resilient force necessary to hold the terminal 80 within the insulating spacer 86. The insulating spacer electrically insulates the terminal 80 from the sleeve 68, the sleeve 68 being in electrically conductive engagement with the sleeve 22. Thus, for the embodiment shown, the sleeve 22 forms one terminal of the sensor and the terminal 80 forms the other.

As stated above, it is necessary to provide a reference oxygen partial pressure to the interior of the electrolyte element 30. In the particular sensor shown, the reference oxygen partial pressure is provided by ambient air, the ambient air entering the interior of the sleeve 68 through a plurality of apertures 90. This air is supplied to the interior surface 34 through the central bore 64. As stated above, in the absence of any protection, road splash and other contaminants may enter the sensor 20 through the aperture 90 due to the fact that the upper end of the sensor is mounted on the exterior surface of the exhaust system. In order to preclude or alleviate such contaminants from entering the interior of the sensor 20, a clip element 92 is placed around the upper end of the sleeve 68 to, at least partially, mask the aperture 90. It is to be understood that the clip number 92 is sufficiently out of round in the area of the aperture 90 to permit air to enter the aperture 90 between the sleeve 68 and the clip number 92.

The sleeve 22 forms one terminal of the gas sensor 20, the sleeve 22 being in electrical contact with the exhaust system and thus the chassis of the vehicle. In order to provide a second, parallel ground terminal, a conductor 94 is provided in a raised tubular portion 96 of the clip 92. The conductive member 94 is held within the portion 96 either by spring tension or may be suitably soldered or otherwise fastened to the portion 96. Similarly, the clip 92 may be soldered to the sleeve 68 or spring tension may be utilized to hold the clip 92 on the sleeve 68.

Thus, it is seen that the sensor 20 is provided with ambient air to the interior surface 34 of the electrolyte element 30 while substantially precluding or alleviating the possibility of contaminants entering the interior of the sleeve 68 and thus contaminate the surface 34. A further description of the other figures of the drawings will illustrate modified forms of clip 92.

Figure 3:
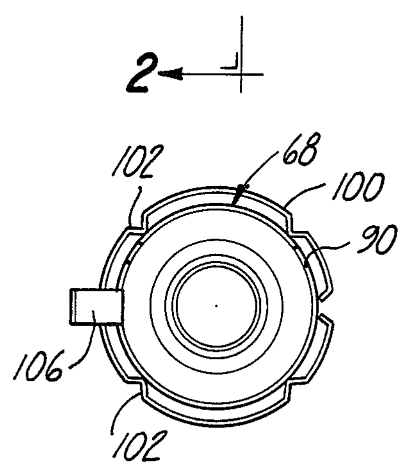
FIG. 3 is a top view of a modified form of the invention of FIG. 1 and particularly illustrating a modified configuration of the protective clip as attached to the oxygen sensor.
Figure 4:
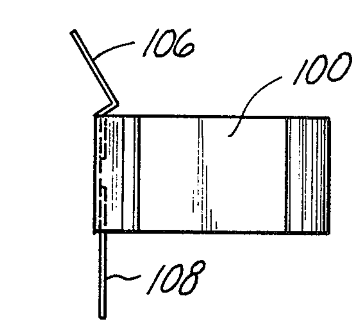
FIG. 4 is a side view of the modified clip of FIG. 3 with the oxygen sensor removed.

Referring now to FIGS. 3 and 4, there is seen to be illustrated a modification of the clip 92 in the form of a clip 100 with a plurality of detents 102 engaging the exterior surface of the sleeve 68 which is fabricated. As was the case with the sensor of FIGS. 1 and 2, a plurality of apertures 90 are provided to permit the entrance of ambient air into the interior of the housing 68. The clip 100 includes a pair of tabs 106, 108 which are suitably attached to the clip 100, as for example by welding or soldering. It is to be understood that the tabs 106, 108 may be stamped as an integral part of the clip 100 and suitably bent to form the shape shown. An external conductor may be attached to the tab 106 and the tab 108 provides additional electrical contact with the sleeve 68. The tab 108 may be welded or soldered to the sleeve 68 or spring contact may be relied on to provide the necessary electrical contact.

Figure 5:
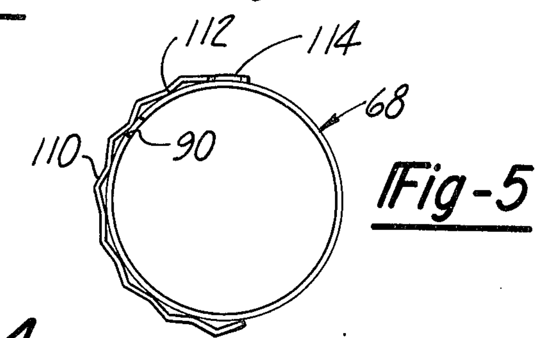
FIG. 5 is a top view of a further modified form of the clip of FIG. 1 with the sensor removed but illustrating the protective sleeve.
Figure 6:
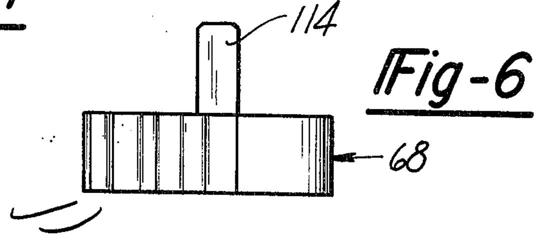
FIG. 6 is a side view of the modified clip of FIG. 5.

Referring to FIGS. 5 and 6, there is seen a further modification of the clips of FIGS. 1 to 4. A clip 110 is again provided with detent portions 112 which are mechanically in contact with the housing 68 and provide the electrical connection between the clip 110 and the sleeve 68. In the case of the clip of FIGS. 5 and 6, a single tab 114 is provided to provide the additional terminal for a ground connection corresponding to the function of tab 106. The clip 110 does not substantially surround the sleeve 68 as was the case with clips 92 and 100 but rather encompasses slightly over one-half of the circumference of the sleeve 68 to provide the necessary spring tension to hold the clip 110 on sleeve 68. Also, the clip 110 may be soldered to the sleeve 68. The sleeve 110 is only required to be a sufficient circumference to mask all of the holes 90 formed in sleeve 68.

Figure 7:
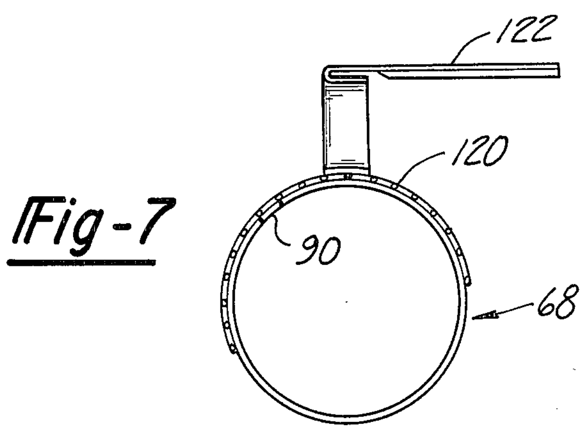
FIG. 7 is a top view of a wire mesh in substitution for the clip of FIG. 1 with a substantial portion of the oxygen sensor removed with the exception of the protective sleeve.
Figure 8:
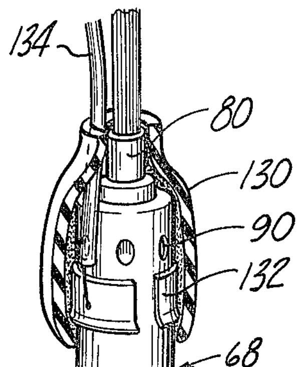
FIG. 8 is a side view of the wire mesh of FIG. 7.
Figure 8:
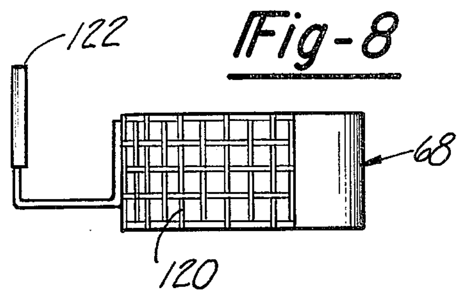

Referring now to FIGS. 7 and 8, there is illustrated a further modification of the clip of the present invention, which modification takes the form of a wire screen or mesh element 120, the mesh having attached thereto a tab terminal 122. The mesh is utilized to mask the aperture 90 and at least partially surrounds the sleeve 68. The mesh is attached to the sleeve 68 by soldering.

FIGS. 9 through 12 illustrate various methods of providing an additional ground terminal for grounding the sensor 20 in addition to the ground provided by the engagement between the shell 22 and the exhaust system of the internal combustion engine.

Figure 9:
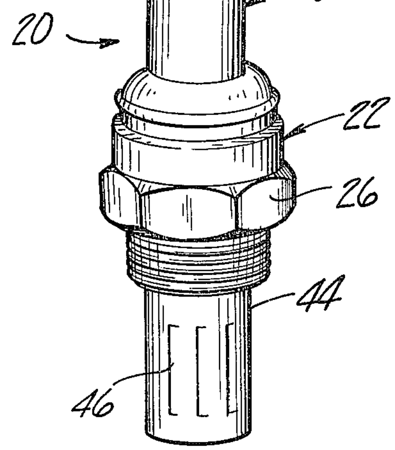
FIG. 9 is a perspective view, partially broken away, of the oxygen sensor configuration of FIG. 1 but illustrating a modified form of the clip which is utilized as a grounding terminal and illustrating a protective boot covering the sleeve apertures.

Referring particularly to FIG. 9, there is provided a silicon rubber boot 130, which is similar to that provided on the above referenced U.S. Pat. No. 3,960,693. The boot 130 is utilized to preclude contaminants from entering apertures 90 formed within the sleeve 68. Within the confines of the boot is provided a grounding clip 132, to which is attached, by soldering, a grounding conductor 134. Thus, the conductor 134 provides an additional ground for the exterior surface of the electrolyte element 30 contained within the shell 22.

Figure 10:
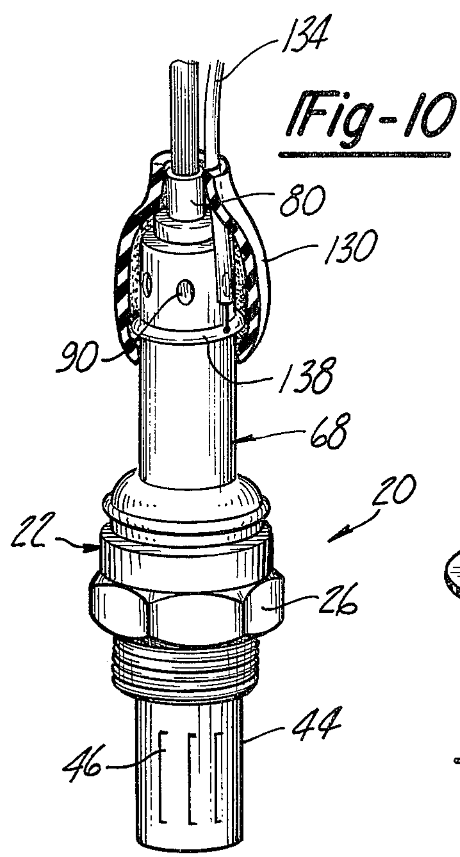
FIG. 10 is another perspective view illustrating the oxygen sensor of FIG. 9 with a modified form of the grounding terminal clip shown thereof.

FIG. 10 illustrates a sensor assembly similar to that illustrated in FIG. 9, and includes the silicone rubber boot 130. However, the clip 132 of FIG. 9 is replaced with a wire element 138 to which is attached the conductor 134. The wire element 138 may be press-fitted over the sleeve 68 or may be soldered thereto to form the electrical connection between the conductor 134 and sleeve 68.

Figure 12:
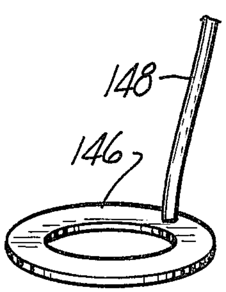
FIG. 12 is a perspective view of the washer of FIG. 11 with the oxygen sensor removed.
Figure 11:
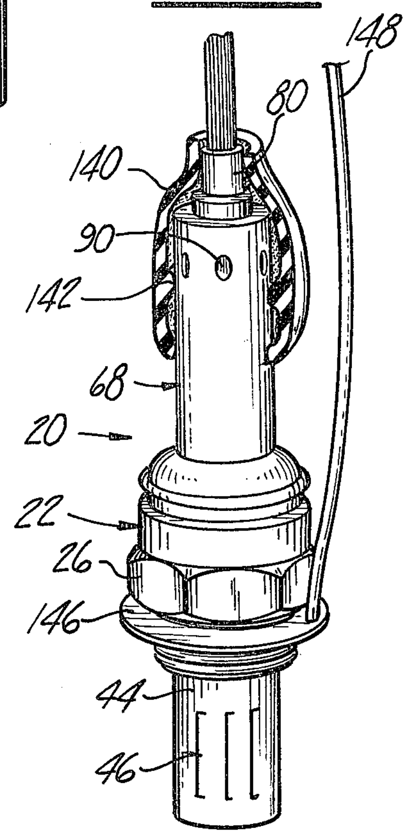
FIG. 11 is a perspective view similar to that of FIG. 9 with the clip removed but illustrating a modified form of round washer.

FIGS. 11 and 12 illustrate a still modification of the additional ground terminal assembly, the sensor 20 is being provided with a modified silicon rubber boot 140 having a detent portion 142. The detent portion 142 provides an additional seal between the boot 140 and the housing sleeve 68 to provide further protection from contaminants entering the sleeve 68 through apertures 90. The sensor 20 is provided a ground element 146, the element 146 preferably taking the form of a washer similar to that used in conjunction with seating spark plugs into an engine. A ground conductor 148 is attached to the washer 146, as for example by soldering. Thus, a simple inexpensive additional ground terminal has been provided utilizing readily available parts which need not be specifically fabricated over and above those fabricated for the use in conjunction with seating spark plugs.

While it will be apparent that the embodiments of the invention herein disclosed are well calculated to fulfill the objects of the invention, it will be appreciated that the invention is susceptible to modification, variation and change without departing from the proper scope or fair meaning of the subjoined claims.

What is claimed is:

1. An electrochemical gas constituent sensor assembly comprising a solid electrolyte sensing element, said sensing element being generally cup-shaped having a closed end and an open end, said sensing element including an interior surface and an exterior surface, said exterior surface being adapted to be exposed to a gas to be sensed and said interior surface being adapted to be exposed to a reference gas, sleeve means forming a cavity in fluid communication with said open end and said interior surface, said sleeve means including aperture means in the wall thereof for communicating the reference gas outside said cavity to the inside of said cavity, and mask means wholly positioned intermediate the ends of said sleeve means for at least partially masking said aperture for substantially precluding the entry of contaminants into said cavity through said aperture.

2. The sensor assembly of claim 1 wherein said mask means is a metallic clip having sufficient circumferential length to mask the entirety of said aperture means.

3. The sensor assembly of claim 2 wherein said clip includes a section thereof radially spaced from said sleeve means.

4. The sensor assembly of claim 3 wherein said clip is formed with at least one detent portion for radially spacing said section.

5. The sensor assembly of claim 4 wherein said clip includes terminal means having a conductor attached thereto forming a terminal of said sensor assembly.

6. The sensor assembly of claim 5 wherein said terminal means is formed as an integral part of said clip and radially extending therefrom.

7. The sensor assembly of claim 5 wherein said terminal means is a tab extending from said clip.

8. The sensor assembly of claim 1 wherein said mask means is formed of spring like material and is of sufficient circumferential length to resiliently fix said clip on said sleeve means.

9. The sensor assembly of claim 1 wherein said mask means is a wire mesh masking said aperture means.

10. The sensor assembly of claim 9 further including terminal means attached to said wire mesh forming a terminal for said sensor assembly.

11. The sensor assembly of claim 1 wherein said mask means is metallic.

12. An electrochemical gas constituent sensor assembly comprising a solid electrolyte sensing element, having an interior surface and an exterior surface, said exterior surface being adapted to be exposed to a gas to be sensed and said interior surface being adapted to be exposed to a reference gas, sleeve means forming a cavity in fluid communication with said open end and said interior surface, said sleeve means including aperture means in the wall thereof for communicating the reference gas outside said cavity to the inside of said cavity, and metallic ground means including a clip positioned on said sleeve means intermediate the ends thereof and in electrical contact therewith, said ground means including a conductor mechanically and electrically connected to said clip.

13. The sensor assembly of claim 12 further including a shell supporting said sensing element, said shell being in electrical contact with the exterior of said sensing element and said sleeve means and forming a second ground for said sensor assembly.

14. The sensor assembly of claim 13 wherein said clip is formed as a generally circular wire element.

15. The sensor assembly of claim 13 wherein said clip is formed as a strap element having an axial dimension greater than the radial dimension.

16. The sensor assembly of claim 13 further including a flexible boot positioned on the end of said sleeve means covering said aperture means and said clip.

* * * * *